(12) United States Patent
Demharter et al.

(10) Patent No.: US 8,380,292 B2
(45) Date of Patent: Feb. 19, 2013

(54) METHOD FOR CHECKING ECG SIGNALS AND ECG MEASURING DEVICE

(75) Inventors: Nikolaus Demharter, Dormitz (DE); Michael Frank, Erlangen (DE); Sven Heggen, Erlangen (DE); Jürgen Rößler, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 265 days.

(21) Appl. No.: 12/482,710

(22) Filed: Jun. 11, 2009

(65) Prior Publication Data
US 2009/0318821 A1    Dec. 24, 2009

(30) Foreign Application Priority Data
Jun. 19, 2008  (DE) .......................... 10 2008 029 173

(51) Int. Cl.
*A61B 5/04* (2006.01)
*A61N 1/00* (2006.01)

(52) U.S. Cl. ................ 600/509; 600/524; 607/4; 607/5; 607/14

(58) Field of Classification Search .................. 600/509, 600/524; 607/4–5, 14
See application file for complete search history.

(56) References Cited

U.S. PATENT DOCUMENTS

| | | | |
|---|---|---|---|
| 7,787,941 B2* | 8/2010 | Boese et al. ................... | 600/509 |
| 2005/0197586 A1* | 9/2005 | Pearlman ...................... | 600/509 |
| 2007/0038257 A1 | 2/2007 | Gray | |
| 2007/0167850 A1* | 7/2007 | Russell et al. ................. | 600/513 |

FOREIGN PATENT DOCUMENTS
DE   10 2005 027 438 A1   12/2006

* cited by examiner

Primary Examiner — Nicole F Lavert

(57) ABSTRACT

The invention relates to a method for checking ECG signals measured by an ECG measuring device having at least three electrodes for the presence of interference errors. At least three voltages are measured on a closed circulation path across the electrodes of the ECG measuring device. A monitoring value is calculated from the three measured voltages. A presence of an error is checked by determining a deviation of the monitoring value from a reference value. An error signal is outputted if an error is presented. The ECG measuring device has a further processing unit for processing voltage signals between a different pair of electrodes and a monitoring unit for calculating the monitoring value.

12 Claims, 1 Drawing Sheet

METHOD FOR CHECKING ECG SIGNALS AND ECG MEASURING DEVICE

CROSS REFERENCE TO RELATED APPLICATIONS

This application claims priority of German application No. 10 2008 029 173.0 filed Jun. 19, 2008, which is incorporated by reference herein in its entirety.

FIELD OF THE INVENTION

The invention relates to a method for checking ECG signals and to an ECG measuring device.

BACKGROUND OF THE INVENTION

ECG measuring devices are primarily used for measuring and monitoring a patient's cardiac function. To that end the summation voltage of the electrical activity of the myocardial fibers is typically measured across at least two electrodes as what is referred to as an "ECG signal".

There are further applications still, however. For example, ECG signals are also used in medical imaging for the purpose of generating trigger signals. During imaging, the ECG signal is used to acquire information about the cardiac cycle in order thereby to synchronize the imaging with the activity of the heart. In particular with imaging methods that require a relatively long recording time, high-quality images of the heart or also images of regions that are moved by the heartbeat can be recorded in this way.

ECG measuring devices are also used for recording ECG signals during an examination of a patient by means of a magnetic resonance scanner. In this case, however, operation in the magnetic resonance scanner places particular requirements on the ECG measuring device due to the strong gradient fields and radio-frequency fields used for imaging in the scanner, in order to prevent mutual interference between magnetic resonance scanner and ECG measuring device. ECG measuring devices which are magnetic resonance compatible in the sense referred to above are available on the market.

However, a continuing major problem for reliable ECG signal measurement are magnetic fields that change over time, as used in the magnetic resonance scanner as magnetic gradient fields for position encoding. According to the law of induction, temporally fluctuating magnetic fields of this type generate interference voltages which are coupled into the ECG signal recorded by the ECG electrodes as noise. A further source of induced interferences of said kind are movements of the ECG measuring device in the static magnetic field of a magnetic resonance scanner. Such magnetically generated interference signals are superimposed on the ECG signal generated by the heart and distort said signal.

These interference sources are extremely undesirable. Synchronizing a recording of a magnetic resonance image with the heartbeat requires reliable detection of the R wave of the ECG signal. Due to their often similar shape, for example, the interference signals can erroneously be interpreted as an R wave and consequently can incorrectly initiate a triggering of a recording of a magnetic resonance image. On the other hand it can also happen that a "real" R wave is not recognized as such because of the superimposed interference signals. This frequently leads to a significant deterioration in image quality.

In the prior art, attempts have been made to avoid incorrect triggerings of said kind by deductions based on an analysis of the amplitudes and dynamics of the ECG signals.

Further sources of errors in ECG signals can be due to the manner in which an ECG measuring device used is installed and set up. For example, a loose connection or a break in an electrode cable may be present.

SUMMARY OF THE INVENTION

The object underlying the invention is thus to disclose an ECG measuring arrangement and a method which in each case permit reliable detection of interference affecting measured ECG signals and in which the risk of emitting incorrect trigger signals is reduced.

The foregoing object is achieved by a method and by a device as claimed in the claims.

In this case the inventive method for checking ECG signals measured by means of an ECG measuring device comprising at least three electrodes for the presence of interference errors comprises the following steps:
- measure at least three voltages measured on a closed circulation path across the electrodes of the ECG measuring device,
- calculate a monitoring value from the at least three measured voltages,
- establish the presence of an error by determining a deviation of the monitoring value from a reference value,
- output an error state signal.

The method permits interference errors in ECG signals to be detected with particularly low overhead. On the one hand it is thus possible to suppress incorrect triggerings of magnetic resonance image recordings which were caused by interference-affected ECG signals, thereby resulting in high-quality images being recorded. On the other hand it is possible at the same time to monitor the ECG measuring device as such, in particular its configuration from electrodes, cables etc., using only a small amount of resources.

The inventive ECG measuring device comprises at least three electrodes as well as a farther-processing unit for processing voltage signals arising between a different pair of electrodes in each case, and a monitoring unit which comprises a monitoring value calculation unit by means of which a monitoring value can be determined from at least three voltages measured on a closed circulation path across the electrodes, which monitoring value enables the ECG measuring device to be checked in accordance with an inventive method.

The method-related advantages and embodiments are applicable analogously to the device.

BRIEF DESCRIPTION OF THE DRAWINGS

Further advantages and details of the present invention will emerge from the exemplary embodiments described below as well as with reference to the drawings. The examples described constitute no limitation of the invention.

Figure 1:
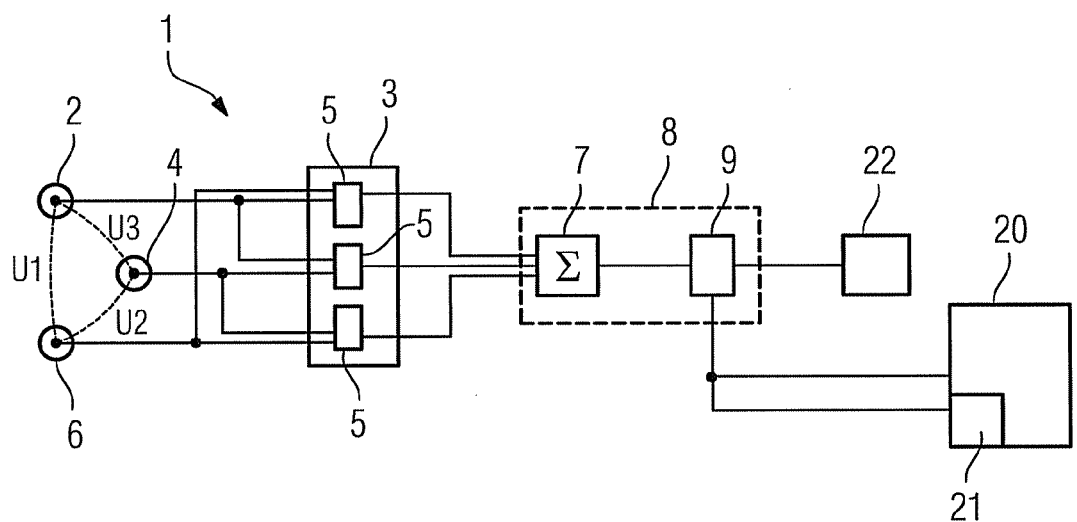

Brief description of the drawings:

FIG. 1 shows an ECG measuring arrangement according to the invention, and

Figure 2:
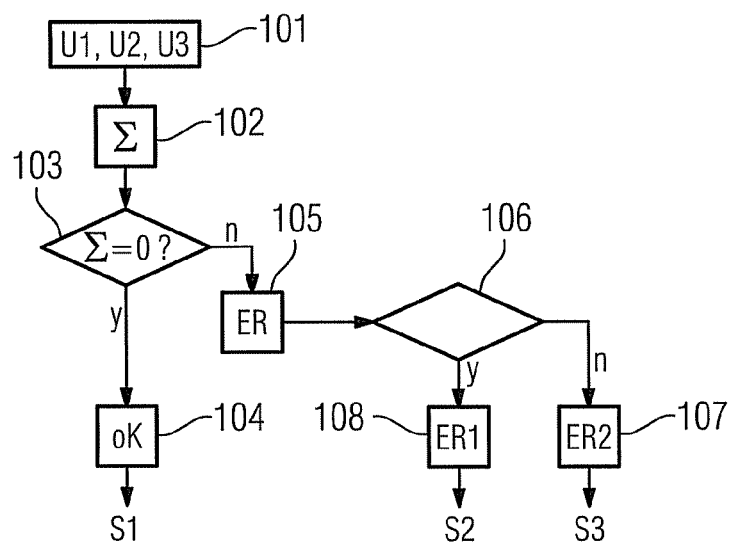

FIG. 2 is a schematic flowchart of a method according to the invention.

DETAILED DESCRIPTION OF THE INVENTION

FIG. 1 shows the parts relevant to the invention of an inventive ECG measuring device 1 having three electrodes 2,4,6 which are attached in a well-known manner to an examination object, for example the thorax of a patient (not shown). The general design of ECG measuring devices, including those for triggering magnetic resonance scanners, is well-known in the prior art and in the interest of better clarity of illustration will not be repeated here.

The voltages U1, U2 and U3 on a closed circulation path across the electrodes 2,4,6, as indicated by the dashed arrows in FIG. 1, can be tapped between each pair of electrodes 2,4,6 of the inventive ECG measuring device 1. In this case the voltages U1,U2,U3 represent the respective derivations of the cardiac electrical potentials, on which interference signals may possibly be superimposed.

In order to measure the voltages U1,U2,U3, electrode cables are routed from the electrodes 2,4,6 into a further-processing unit 3, where the voltages U1,U2,U3 are measured (block 101 in FIG. 2). In this step, the measured values are possibly converted in addition into digital signals by means of one or more digitizer units 5, thereby simplifying the further processing.

The measured values of the voltages U1,U2,U3 are transmitted to a monitoring unit 8. For that purpose the further-processing unit 3 is connected to the monitoring unit 8 by means of at least one signal-conducting connection.

The monitoring unit 8 comprises a monitoring value calculation unit 7 in which a monitoring value is determined from the three measured voltages U1,U2,U3. In an advantageous exemplary embodiment, the monitoring value calculation unit 7 is a summation unit which calculates the sum of the measured values of the voltages U1,U2,U3 as the monitoring value, as shown in block 102 in FIG. 2. This approach proves particularly advantageous, since no additional hardware is necessary for obtaining the summation value, but instead a purely digital embodiment of the monitoring unit 8 is sufficient, in particular when digitized voltage values are used. The method can therefore be implemented without great overhead.

The monitoring value determined by the monitoring value calculation unit 7 is compared with a reference value by a checking unit 9 of the monitoring unit 8 and a deviation of the monitoring value from the reference value determined. If the sum of the measured values of the voltages U1,U2,U3 has been calculated as the monitoring value, the value zero is advantageously used as the reference value, as shown in block 103 in FIG. 2, because by forming the sum of the voltages U1,U2,U3 as the monitoring value and comparing the value of the sum with the value zero as reference value, it can easily be decided, based on Kirchhoff's second rule, whether an interference error is present or not.

Kirchhoff's second rule states that the sum of the voltages of a mesh or, as the case may be, across a closed loop or circulation path must be equal to zero. Thus, if the calculated sum is not equal to zero, an error must be present. Said error can on the one hand be a malfunction in the hardware of the ECG measuring device, e.g. a fault in the cabling or wiring (electrodes, electrode cables, further-processing unit, data transmission . . . ) of the ECG measuring device, or be due to temporally fluctuating magnetic fields, as generated e.g. in the environment of a magnetic resonance scanner due to changing gradient fields or movements in the static magnetic field of the magnetic resonance scanner. For Kirchhoff's second rule, the so-called "mesh rule", applies only in the absence of temporally fluctuating magnetic fields, i.e. the sum of the voltages of a mesh is only equal to zero in the absence of temporally fluctuating magnetic fields.

If the sum of the voltages U1,U2,U3 is not equal to zero, or if the deviation of the monitoring value from the reference value exceeds a predefined tolerance range even though no temporally fluctuating magnetic fields are present, troubleshooting should focus on the hardware of the ECG measuring device.

Thus, the presence of an error can be established by determination of a deviation of the monitoring value from the reference value in block 103.

If the checking unit 9 determines in block 103 that the monitoring value corresponds to the reference value (within the scope of predefined tolerances, where applicable), then there is no error present (block 104 in FIG. 2) and a corresponding error state signal S1 is output by the monitoring unit 8, e.g. in order to be routed to an MR control unit 20 and/or an MR trigger unit 21 (MR: Magnetic Resonance) of a magnetic resonance scanner (not shown) and to acknowledge a trigger signal which has been sent in the customary manner by the ECG measuring device 1 to the magnetic resonance scanner as valid. Toward that end the monitoring unit 8 is advantageously connected in a signal-conducting manner to the MR control unit 20 and/or the MR trigger unit 21.

If the checking unit 9 determines in block 103 that the monitoring value does not correspond to the reference value, an error is present (block 105) and a corresponding error state signal S2,S3 is output by the monitoring unit 8.

Advantageously, the monitoring unit 8 is furthermore embodied for receiving from the MR control unit 20 information concerning the presence of a temporal magnetic field change, e.g. due to radiated magnetic resonance signals received (an MR sequence) and/or a movement, e.g. a displacement of a table on which the ECG measuring device 1 is situated (block 106 in FIG. 2). If the monitoring unit 8 establishes in this way that an interference with ECG signals has occurred that were measured simultaneously with radiated magnetic resonance signals received and/or movements of the ECG measuring device 1 in the static magnetic field of the magnetic resonance scanner (block 108 in FIG. 2), it indicates a magnetic-field-induced error by outputting the error state signal S2. Gradient-induced interference-signal injections in particular can be detected in this way. These are present when an interference signal S2 occurred and the ECG measuring device 1 was not simultaneously moved in the static magnetic field of the magnetic resonance scanner.

The error state signal S2 is advantageously used to suppress a possible triggering by the MR trigger unit 21 of the recording of a magnetic resonance image by means of the magnetic resonance scanner. The described simple way of detecting magnetic-field-induced interference thus permits incorrect triggerings caused by magnetic-field-induced interference to be suppressed without great overhead. Accordingly, a precise triggering of magnetic resonance image recordings by means of ECG signals and hence a high image quality of the recordings can be achieved.

If the monitoring unit 8 establishes in block 106 that no magnetic-field-induced interference is present (block 107), it indicates a malfunction in the hardware of the ECG measuring device 1 by outputting the error state signal S3. The output of an error state signal S3 advantageously leads to a corresponding display for a user on a display device 22. For example, the display can read: "Fault—check ECG hardware". It is thus possible, with little investment of effort or resources, to provide validity checking and monitoring of the hardware of the ECG measuring device, in particular the structure consisting of electrodes 2,4,6, electrode cables, digitizer units 5 and further post-processing units, such as e.g. also the data transmission paths. Alternatively, an error state signal S3 can also be signaled by a flashing of a corresponding indicator light or similar on the display device 22.

Similarly, the outputting of an error state signal S2 or an error state signal S1 can likewise lead to a display on the display device 22. For example, S1->"ok—no fault", S2->"fault—triggering suppressed" or by flashing of corresponding indicator lights.

In the example presented, the ECG measuring device 1 comprises precisely three electrodes 2,4,6. It is self-evident that ECG measuring devices having more than three electrodes are also suitable for performing the method according to the invention.

The invention claimed is:

1. A method for checking error states that can affect an electrocardiogram (ECG) signal measured by an ECG measuring device, which is operatively coupled to a magnetic resonance scanner, the method comprising:
    measuring voltages generated by a heart on an electrically-closed circuit loop across electrodes of the ECG measuring device between different pairs of the electrodes;
    calculating a monitoring value of the voltages generated by the heart from a combination of the measured voltages;
    determining a deviation of the calculated monitoring value of the voltages generated by the heart from a reference value and whether the deviation exceeds the reference value by a predefined amount;
    synchronous with the measuring of voltages generated by the heart, monitoring at least one signal indicative of an operational condition of the magnetic resonance scanner;
    if the deviation of the monitoring value of the voltages generated by the heart exceeds the reference value by the predefined amount and, based on the operational condition of the magnetic resonance scanner, identifying at least an error state due to electromagnetic interference with the monitoring value of the voltages generated by the heart, the electromagnetic interference caused by a temporal change in at least one electromagnetic field generated by the magnetic resonance scanner;
    outputting an error signal indicative of the error state; and
    generating a suppression signal configured to suppress a triggering of the magnetic resonance scanner in response to the ECG signal measured by the ECG measuring device, wherein a suppression of the magnetic resonance scanner by the suppression signal is temporally arranged to avoid recording a magnetic resonance image while the monitoring value of the voltages generated by the heart is subject to deviation which exceeds the reference value by the predefined amount.

2. The method as claimed in claim 1, wherein the measured voltages are digitized before calculating the monitoring value.

3. The method as claimed in claim 1, wherein the monitoring value is a summation of the measured voltages.

4. The method as claimed in claim 1, wherein the error state is selected from the group consisting of a magnetic-field-induced error, a gradient-induced interference-signal injection and a malfunction in a component of the ECG measuring device.

5. The method as claimed in claim 4, wherein the identifying of the error state is defined so that the error signal indicates the magnetic-field-induced error if the ECG signal is measured simultaneously with a magnetic resonance measurement.

6. The method as claimed in claim 4, wherein the identifying of the error state is defined so that the error signal indicates the magnetic-field-induced error if the ECG measuring device moves in a static magnetic field of the magnetic resonance scanner.

7. The method as claimed in claim 4, wherein the identifying of the error state is defined so that the error signal indicates the gradient-induced interference-signal injection if the ECG measuring device does not move in a static magnetic field of the magnetic resonance scanner.

8. The method as claimed in claim 1, wherein the ECG measuring device comprises at least three electrodes.

9. The method as claimed in claim 1, further comprising configuring the error signal to convey a user-readable indication selected from the group consisting of no error state, a triggering suppression and a fault in the ECG hardware.

10. Apparatus to check error states that can affect an electrocardiogram (ECG) signal measured by an ECG measuring device, which is operatively coupled to a magnetic resonance scanner, said apparatus comprising:
    a plurality of electrodes;
    a processing unit configured to measure voltages generated by a heart, and which develop on an electrically-closed circuit loop between different pairs of the electrodes;
    a monitoring unit coupled to the processing unit and to a control unit of the magnetic resonance scanner, the monitoring unit including a monitoring value calculation unit configured to calculate a monitoring value from a combination of the measured voltages, the monitoring unit further including a checking unit coupled to the monitoring value calculation unit, the checking unit configured to:
        determine a deviation of the monitoring value of the voltages generated by the heart from a reference value and whether the deviation exceeds the reference value by a predefined amount;
        synchronous with the measurement of voltages generated by the heart, monitor at least one signal from the control unit of the magnetic resonance scanner, said at least one signal indicative of an operational condition of the magnetic resonance scanner;
        if the deviation of the calculated monitoring value of the voltages generated by the heart exceeds the reference value by the predefined amount and based on the operational condition of the magnetic resonance scanner, identify at least an error state due to electromagnetic interference with the monitoring value of the voltages generated by the heart, the electromagnetic interference caused by a temporal change in at least one electromagnetic field generated by the magnetic resonance scanner;
        output an error signal indicative of the error state;
        generate a suppression signal coupled to a trigger unit to suppress a triggering of the magnetic resonance system in response to the ECG signal measured by the ECG measuring device, wherein a suppression of the magnetic resonance scanner by the suppression signal is temporally arranged to avoid recording a magnetic resonance image while the monitoring value of the voltages generated by the heart is subject to deviation which exceeds the reference value by the predefined amount.

11. The apparatus as claimed in claim 10, wherein the monitoring value calculation unit is a summation unit configured to add the voltages to calculate the monitoring value.

12. The apparatus as claimed in claim 10, wherein a digitizer unit is connected to the monitoring value calculation unit and digitizes the measured voltages before calculating the monitoring value.

* * * * *